United States Patent [19]

Cartmell

[11] Patent Number: 5,005,592

[45] Date of Patent: Apr. 9, 1991

[54] METHOD AND APPARATUS FOR TRACKING CATHETERS

[75] Inventor: Robert L. Cartmell, Bellbrook, Ohio

[73] Assignee: Becton Dickinson and Company, Franklin Lankes, N.J.

[21] Appl. No.: 428,386

[22] Filed: Oct. 27, 1989

[51] Int. Cl.⁵ .............................................. A61B 5/05
[52] U.S. Cl. .............................. 128/899; 128/653 R; 340/870.31
[58] Field of Search .................. 128/631, 653 R, 897, 128/899, 903; 604/280; 340/686, 687, 810.32, 870.33, 870.34

[56] References Cited

U.S. PATENT DOCUMENTS

| | | | |
|---|---|---|---|
| 4,173,228 | 11/1979 | Van Steenwyk et al. | 128/653 R |
| 4,317,078 | 2/1982 | Weed et al. | 128/653 R |
| 4,445,501 | 5/1984 | Bresler | 600/12 |
| 4,905,698 | 3/1990 | Strohl Jr. et al. | 128/653 R |

Primary Examiner—Lee S. Cohen
Assistant Examiner—Kevin Pontius
Attorney, Agent, or Firm—Hoffman & Baron

[57] ABSTRACT

A device for tracking catheters includes an oscillator which is coupled to a transmit coil. The transmit coil is rotated in a direction transverse to the longitudinal axis of the transmit coil. A receive coil situated on the guide wire of a catheter inserted into a patient's body receives the signal transmitted from the transmit coil. A rectifier rectifies the received signal, and a filter filters the rectified received signal. A strobe circuit provides strobes of light in response to the rectifie received signal and co-operates with bar image forming circuitry and structure to provide an image of a bar which is aligned with the longitudinal axis of the receive coil, which is indicative of the orientation of the catheter and guide wire on which the receive coil is situated. A bar display indicates the relative proximity of the transmit coil to the receive coil, and a numeric display provides a read-out of the distance between the transmit coil and the receive coil.

13 Claims, 9 Drawing Sheets

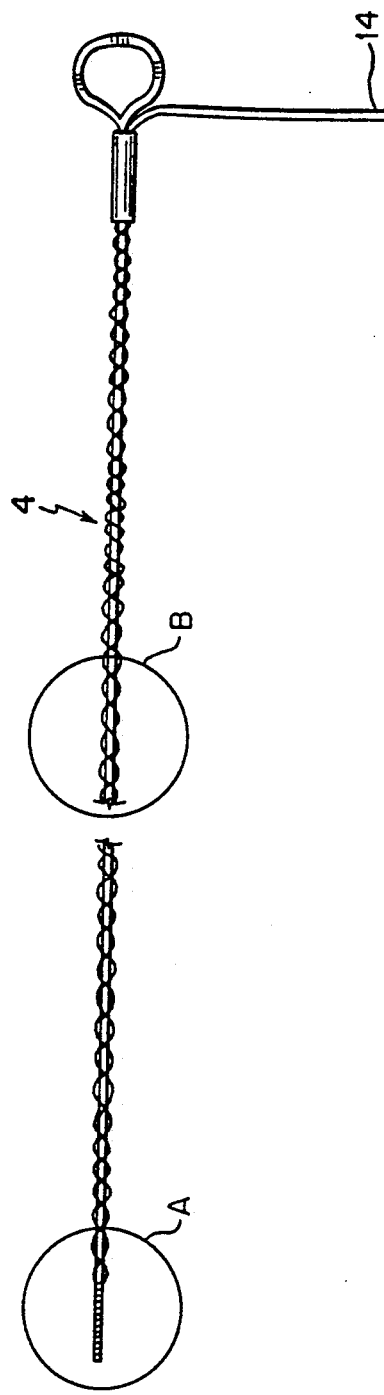
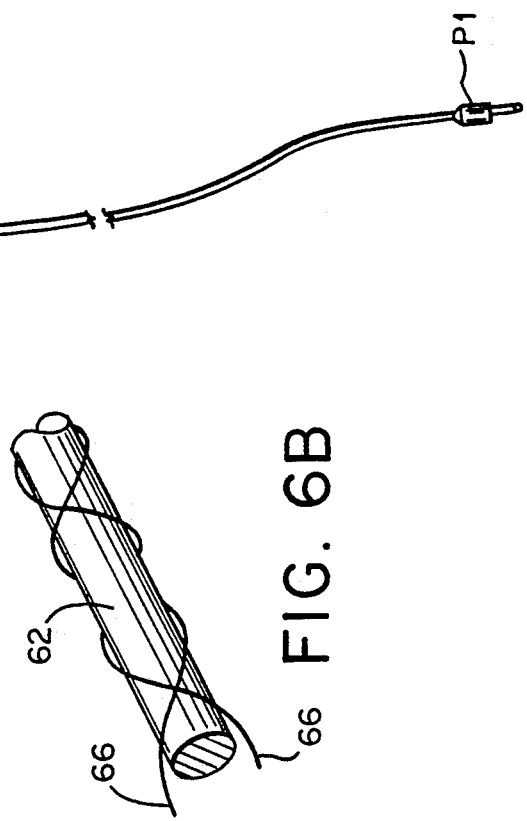
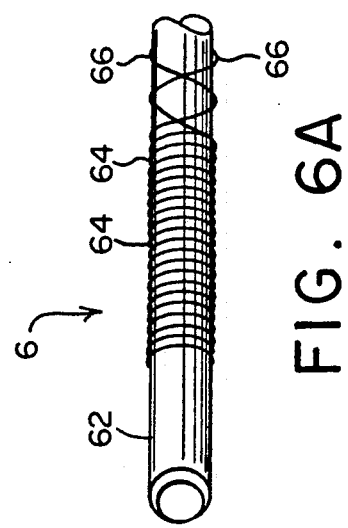
FIG. 5
FIG. 6A
FIG. 6B

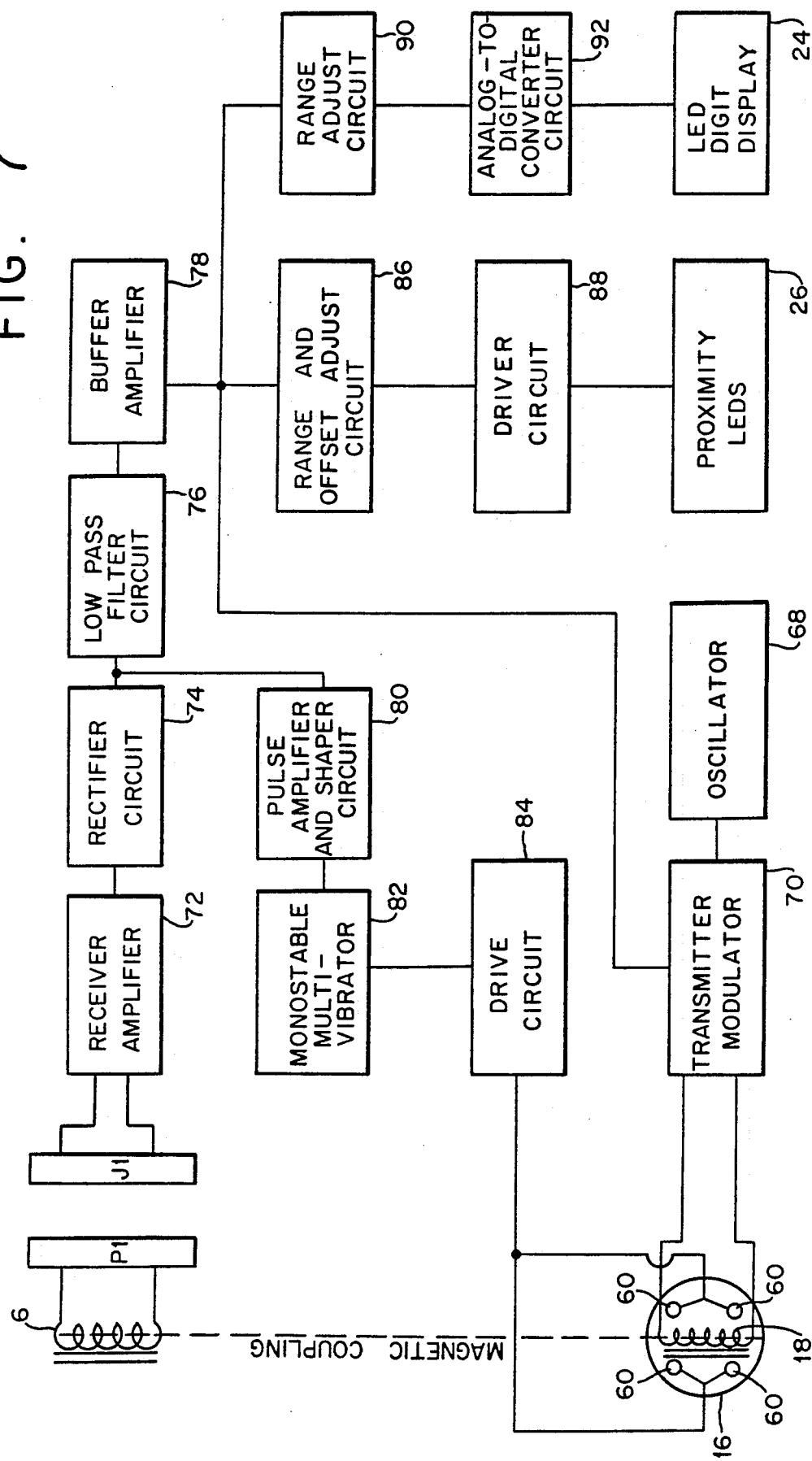

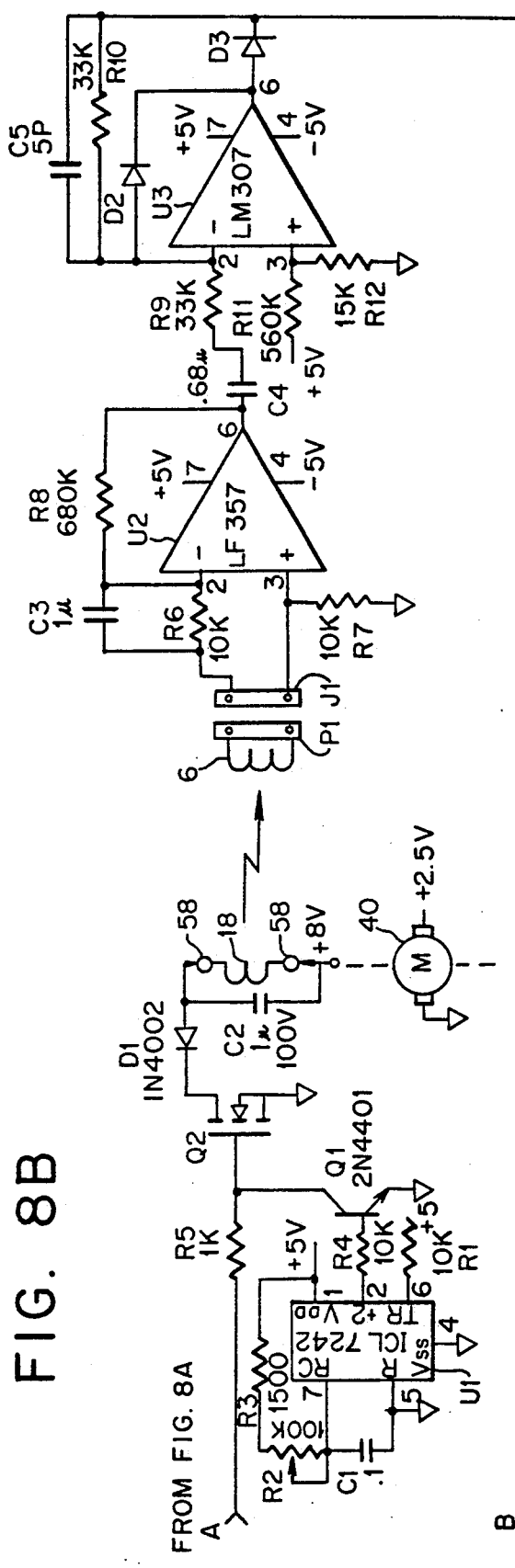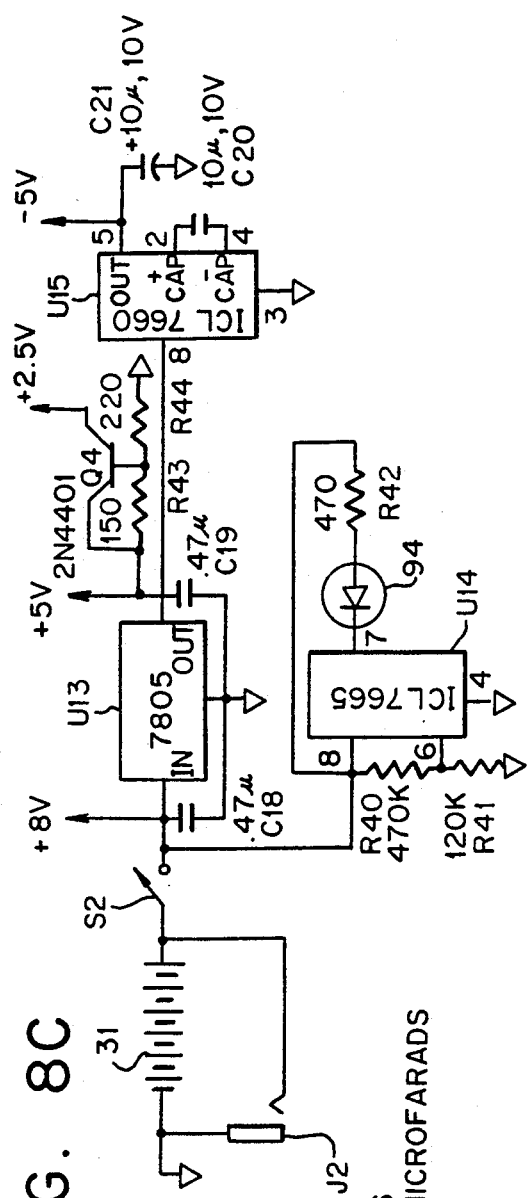
FIG. 8B
FIG. 8C
RESISTOR VALVES ARE IN OHMS
CAPACITOR VALVES ARE IN MICROFARADS

METHOD AND APPARATUS FOR TRACKING CATHETERS

BACKGROUND OF THE INVENTION

1. Field Of The Invention

The present invention relates to medical equipment generally, and more particularly to medical equipment used to aid in the tracking of catheters inserted into a patient's body by indicating the orientation and distance of the catheter in the body.

2. Description Of The Prior Art

The tracking of catheters which have been inserted into a body has been accomplished in the past by a method which required the medical team to first insert a guide wire into the vein or artery in which the catheter would be inserted. The catheter is then led along this guide wire for a predefined distance, such distance being less than the distance required to place the catheter in its intended destination. The patient is x-rayed to determine if the path which the catheter and guide wire has followed is the same as the intended path. If so, the catheter is guided on to its ultimate and final destination. If the path which the guide wire and the catheter have taken is different from the intended path, the catheter and guide wire must be withdrawn and the process repeated. This sequence is repeated until the catheter and guide wire reach the desired destination.

The disadvantages of this process lie in the expense and danger involved in subjecting a patient to repeated x-ray treatment and the delay caused by the need to take x-ray photographs before completing the catheter insertion. Also, the conventional "trial-and-error" method of inserting and tracking a catheter described previously subjects the patient to undue stress.

OBJECTS AND SUMMARY OF THE INVENTION

It is an object of the present invention to provide a means to determine the location and orientation of a medical object which has been inserted into a living body.

It is a further object of the present invention to provide a device which can quickly and accurately determine the position and orientation of a catheter in a body.

It is another object of the present invention to provide a catheter tracer which can determine the distance and orientation of a catheter inserted into a patient's body.

It is yet another object of the present invention to provide a hand-held device for tracking a catheter inserted into a patient's body, which device is simple in construction and inexpensive to manufacture.

It is yet a further object of the present invention to provide the combination of a locator wire which is inserted into the catheter and a catheter tracer adapted to interact with the locator wire in determining the position of the catheter within a body.

It is still another object of a present invention to provide a method and a device for tracking catheters inserted into a body, which method and device overcome the inherent disadvantages of known methods of tracking catheters.

In accordance with one form of the present invention, a catheter tracer basically comprises a transmitter portion and a receiver portion. The transmitter portion is mounted in a hand-held probe and includes an oscillator which generates a carrier frequency signal, and a transmit coil to which the carrier frequency signal is provided.

The transmitter further includes a drive mechanism for rotating the coil at a predetermined rate. Because of the rotation of the coil, the transmitter transmits an amplitude modulated or "pulsating" signal, the signal being modulated at a frequency which is equal to the rotational rate of the coil.

The receiver portion of the catheter tracer includes a receive coil. In one form of the invention, the receive coil is mounted on, or defines, the tip of a catheter or its guide wire adapted to be inserted into a patient's body. Alternatively, the receive coil may be mounted on the end of a "locator" wire. The catheter guide wire is removed and the locator wire is inserted into the catheter in its place when determining the position of the catheter.

As the transmit coil is rotated, a time varying, pulsating current and voltage signal is electromagnetically induced in the receive coil. The amplitude of the received signal is greatest when, for a given distance between the two coils, the longitudinal axis of the transmit coil is aligned with the longitudinal axis of the receive coil. This relationship between the two coils will help identify the orientation of the receive coil and, correspondingly, the location and direction of the catheter.

The receiver has additional circuitry for processing the signal induced in the receive coil. This additional circuitry is carried in the hand-held probe with the transmitter. The processing circuitry of the receiver includes a differential amplifier which is coupled to the receive coil and which amplifies the received signal. The output signal of this amplifier is provided to a rectifier circuit, which rectifies the amplifier's output signal.

The receiver processing circuitry further includes a low pass filter or integrator circuit, which receives the rectified output signal of the rectifier circuit and provides an output signal which is, essentially, a voltage level having an amplitude which varies with the peak amplitude of the rectified output signal.

The catheter tracer of the present invention also includes a bar display circuit and a digital voltmeter circuit, each of which is provided with the filter output signal. The bar display circuit includes a bar display mounted on the hand-held probe, which bar display provides the physician with an indication of the relative strength of the signal received and, accordingly, the relative proximity of the probe to the catheter. The digital voltmeter circuit includes a numeric display, which display provides the physician with a numeric indication of the distance between the rotating transmit coil in the handheld probe and the receive coil mounted on the catheter, its guide wire or the locator wire.

The catheter tracer further includes circuitry and an associated display for indicating to the physician the orientation of the catheter, guide wire or locator wire within the patient's body. The catheter orientation circuitry effectively translates the time relation of the amplitude peaks of the received signal into a display of the orientation of the receive coil mounted on the catheter, locator wire or guide wire tip. The orientation circuitry includes a pulse amplifier and shaper circuit which is provided with the output signal of the rectifier circuit. The pulse amplifier and shaper circuit provides gain and an offset adjustment to the rectified signal, and eliminates the 2,200 Hertz carrier frequency from the signal. The output signal from the pulse amplifier and shaper circuit is, effectively, the amplified envelope of the rectified signal, adjustable in offset. The output signal of the pulse amplifier and shaper circuit is provided to a monostable multivibrator and is adjusted in offset to trigger the monostable multivibrator at the peaks of the envelope, which correspond to the peaks in the received signal. The multivibrator provides a logic output signal in the form of a pulse each time a peak in the received signal occurs.

The output signal of the monostable multivibrator is connected to a drive circuit, which in turn drives light emitting diodes (LEDs). The LEDs are, in effect, strobed on for a predetermined duration whenever a pulse is generated by the monostable multivibrator.

The hand-held probe includes an essentially opaque template which includes a diametrically extending slot. The slotted template rotates synchronously with the rotating transmit coil, with the slot being in alignment lengthwise with the longitudinal axis of the transmit coil. The LEDs are arranged in a circle spaced apart from each other and positioned below the slotted template. Whenever the LEDs are strobed on, they project light through the slot in the rotating template. The slot projects the image of a bar or line on a translucent face lens on the probe and above the rotating slotted template so that the image is viewable through the lens by the physician.

As mentioned previously, the amplitude of the received signal is greatest when the longitudinal axis of the transmit coil is aligned with the longitudinal axis of the receive coil. It is at these times of coil alignment that the LEDs are strobed, and their light is projected through the template slot to form the bar image on the lens. Accordingly, the direction of the bar image will correspond to the longitudinal axis of the receive coil, and thus will be indicative of the orientation of the catheter, locator wire or guide wire on which the receive coil is mounted.

A preferred form of the catheter tracer, as well as other embodiments, objects, features and advantages of this invention, will be apparent from the following detailed description of illustrative embodiments thereof, which is to be read in connection with the accompanying drawings.

BRIEF DESCRIPTION OF THE DRAWINGS

FIG. 5 is a cross-sectional view of a locator wire of a catheter, formed in accordance with the present invention.

FIG. 6a is an enlarged perspective view of a portion of the locator wire shown in FIG. 5 and shown encircled by circle A.

FIG. 6b is an enlarged perspective view of a portion of the locator wire shown in FIG. 5 and shown encircled by circle B.

FIG. 7 is a block diagram of an electronic circuit used in the catheter tracer of the present invention.

FIGS. 8a through 8c are schematic diagrams of the circuit used in the catheter tracer of the present invention.

DETAILED DESCRIPTION OF THE PREFERRED EMBODIMENTS

Figure 1:
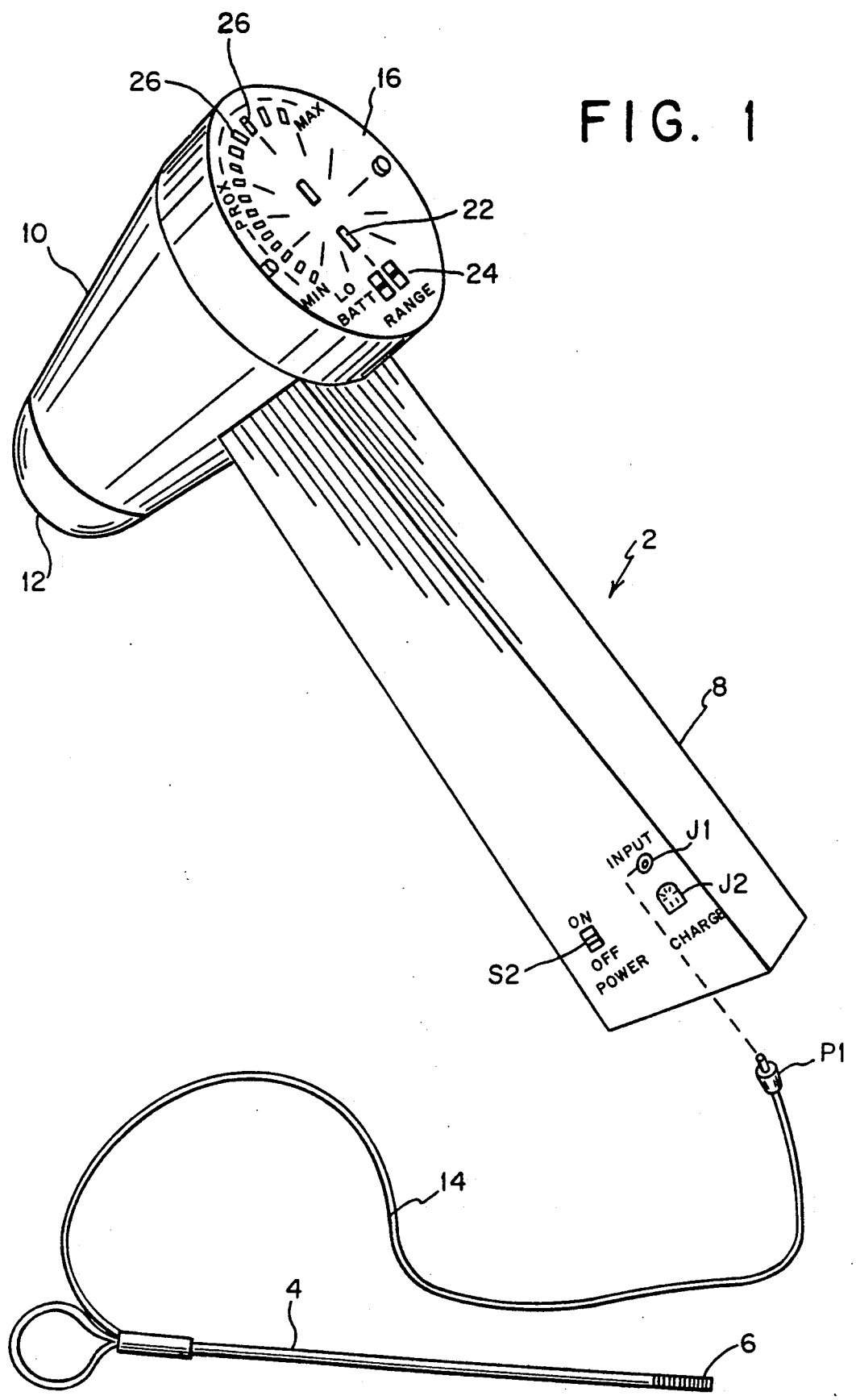
FIG. 1 is a perspective view of the combination of a catheter tracer and a locator wire for a catheter, formed in accordance with one form of the present invention.

Apparatus for tracking a catheter in a patient's body, or hereinafter referred to as a "catheter tracer", formed in accordance with the present invention, is constructed basically in two interconnectable parts: 1) a hand-held probe 2; and 2) a locator wire 4 constructed to include a receive coil 6, as will be described.

The probe 2 has a shape which allows for easily handling. It includes a handle 8 which is held by the physician, and an enlarged portion or head 10 situated opposite the handle, which head 10 includes a rounded lower portion 12 which is placed over the patient's body near the area which is suspected to contain the tip of the catheter guide wire 4 on which the receive coil 6 is mounted.

The receive coil 6, which may be mounted on the catheter itself, its guide wire or the catheter locator wire 4, as shown in FIG. 1, is connected to the hand-held probe by an electrical conduit 14. This conduit 14 carries the signal which is received by the receive coil to the hand-held probe 2 for processing and for display on its face, as will be described below.

Figure 2:
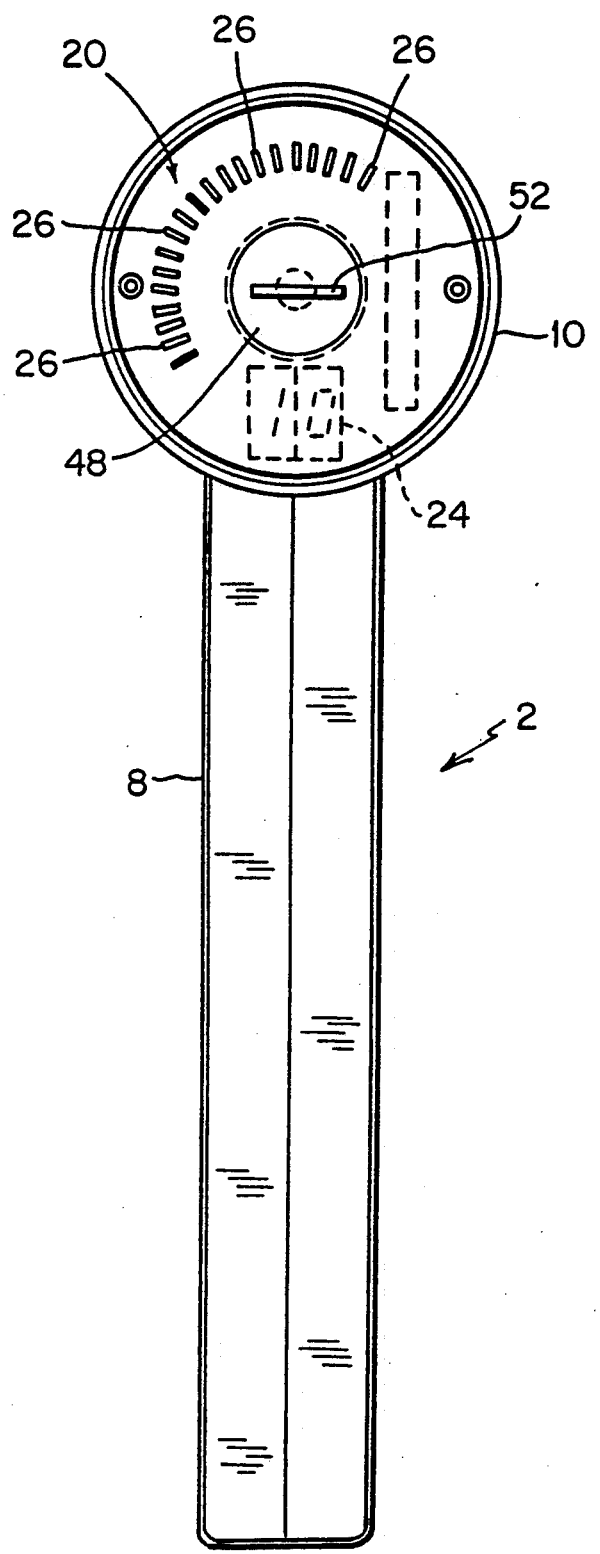
FIG. 2 is a top view of a hand-held probe forming a portion of the catheter tracer of the present invention.

As shown in FIG. 2, the hand-held probe includes a translucent face lens 16 on the enlarged head portion 10 of the probe on a side opposite to the rounded lower portion 12. The face lens 16 of the hand-held probe, which is viewable to the physician, displays three forms of information: 1) distance in centimeters between the rounded lower portion 12 of the probe (in which a transmit coil 18 is located) and the receive coil 6 mounted on the tip of the catheter locator wire; 2) coarse proximity information in the form of a bar graph display 20, which the physician relies on in locating the tip of the catheter, the number of lights of the bar graph display 20 which are illuminated being proportional to the receiver signal strength; and 3) the orientation of the catheter, displayed as an illuminated bar or line 22 on the central portion of the face lens 16 of the hand-held probe.

In the preferred form of the invention, the indicator which displays the distance from the hand-held probe 2 to the tip of the catheter, guide wire or locator wire 4 is in the form of two numeric display LEDs 24 which are mounted side-by-side for the purpose of giving a two digit display of distance in centimeters. The two digit display 24 is centered along the longitudinal axis of the hand-held probe 2 under the face lens 16 of the head portion, and each digit of the display is preferably oriented with its bottom toward the probe handle 8.

The proximity display 20, which indicates the receiver signal strength, is preferably formed of twenty LEDs 26 which are arranged arcuately spaced just under the face lens of the hand-held probe, that is, in a curved bar graph style array.

Figure 3:
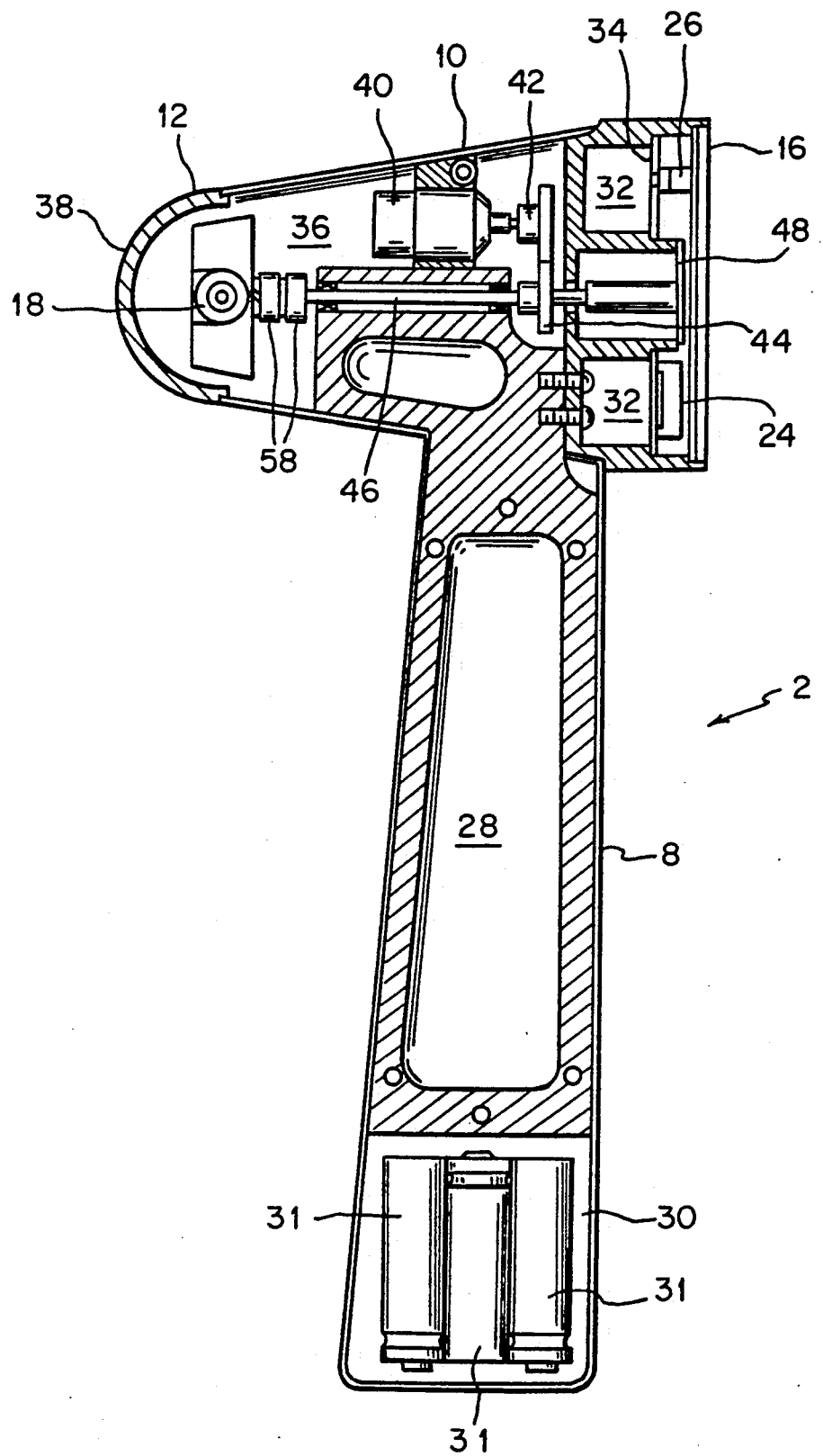
FIG. 3 is a cross-sectional view of the hand-held probe shown in FIG. 2, taken along line 3—3 of FIG. 2.

As shown in FIG. 3 of the drawings, the hand-held probe 2 defines a first chamber 28 in the handle portion 8 of the probe, which chamber 28 houses two printed circuit boards containing the electronic circuitry of the transmitter and receiver portions of the catheter tracer, a second chamber 30 situated at the free end of the handle 8, which chamber 30 preferably houses six nickel cadmium batteries 31 shown double-stacked three high, a third chamber 32 in the head 10 of the probe for receiving a third circular shaped printed circuit board 34 containing the display circuitry, and a fourth chamber 36 in which the mechanical parts and gearing of the catheter tracer are housed. The rounded lower portion 12 of the probe is formed with a plastic or rubber covering or "radome".

Figure 4:
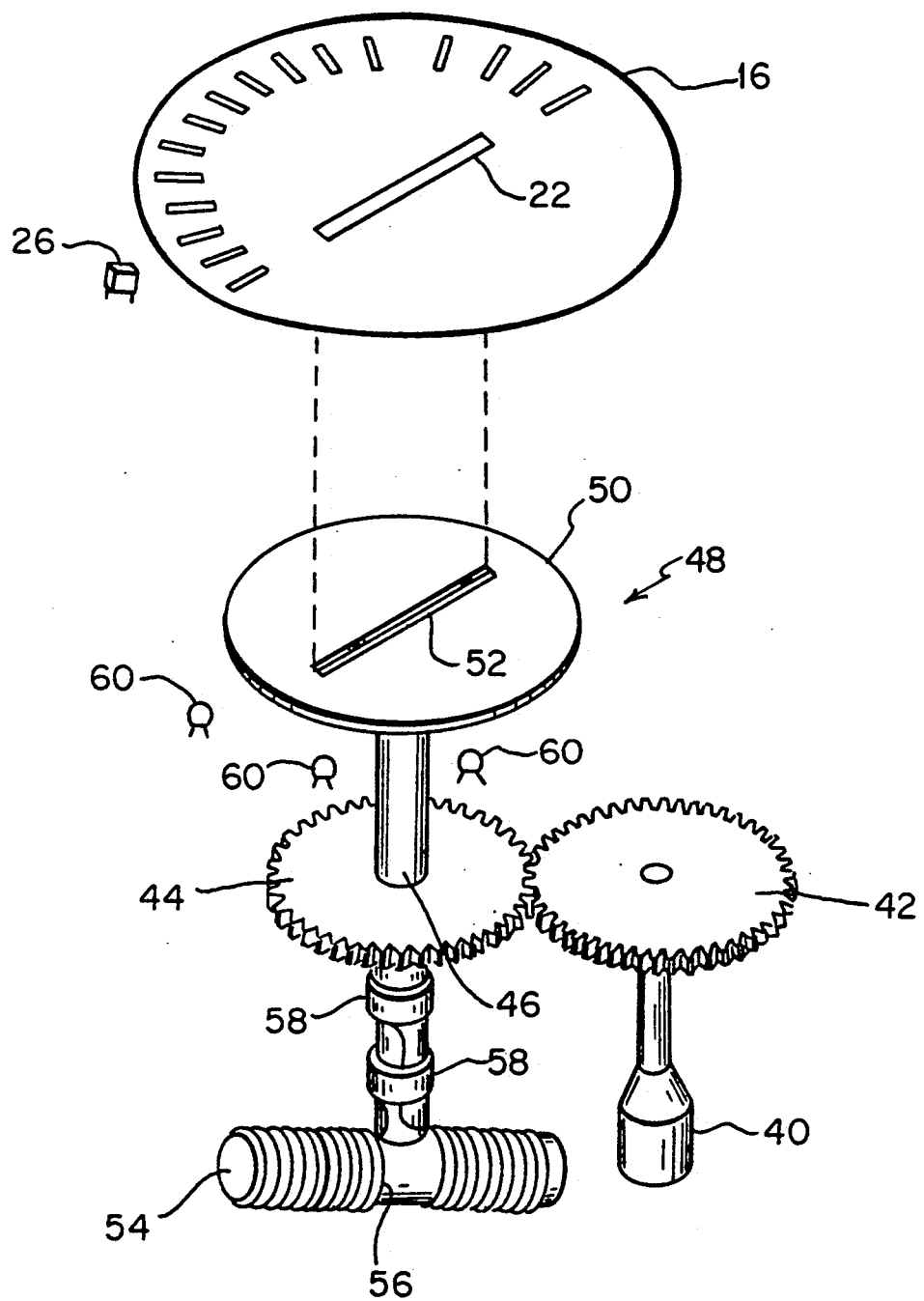
FIG. 4 is an exploded view of the gearing and other mechanical parts housed within the hand-held probe.

The mechanical parts and gearing of the catheter tracer of the present invention is shown in FIG. 3 and in the exploded view of FIG. 4. The mechanical portion of the catheter tracer includes a gear motor 40, which rotates at between about 200 and about 300 r.p.m. Mounted on the shaft of the motor 40 is a main drive gear 42. The main drive gear 42 engages a secondary drive gear 44. The secondary drive gear 44 is fixedly mounted on a secondary drive shaft 46 which extends upwardly through the head 10 of the hand-held probe between the face lens 16 and the rounded lower portion 12.

On one end of the secondary drive shaft 46 is mounted a slotted template 48. The slotted template 48 includes a disc portion 50 having a slot 52 extending partially diametrically across the disc and through the thickness of the disc. The template 48 is formed of an opaque material so that light can only be transmitted through the slot 52.

A transmit coil 18 is mounted on the other end of the secondary drive shaft 46. The transit coil 18 is formed of a ferrous core or support 54 which is disposed with its longitudinal axis perpendicular to the axis of the secondary drive shaft 46. A continuous length of wire 56 is wound about the oppositely extending legs of the core 54 to define the coil, which is formed, effectively, as a Miller coil. More specifically, the transmit coil 18 is preferably formed by layer winding #26 AWG wire on a Miller ferrite core #2006 until its finished dimensions are $\frac{3}{4}$" in length and $\frac{1}{2}$" in diameter. Such a winding should provide a D.C. resistance of about 1.10 ohms, an inductance of 2.2 Mh and a Q of 10. With a 1 microfarad capacitor in parallel with it, the transmit coil 18 should resonate at about 2200 Hertz. The secondary drive shaft 46 intersects the core of the transmit coil 18 at its center so that the transmit coil is balanced as it rotates.

When the motor 40 is energized, its main drive gear 42 engages the secondary drive gear 44, causing the secondary drive shaft 46 to rotate. This in turn causes the transmit coil 18 and the slotted template 48 to rotate in synchronism. The slotted template 48 is arranged relative to the transmit coil 18 such that the longitudinal axis of the slot 52 is aligned with the longitudinal axis of the transmit coil.

A pair of slip rings 58 are provided on the secondary drive shaft 46. Each slip ring 58 is connected to a respective end of the transmit coil lead wire. A pair of contacts (not shown) engage the slip rings 58 and are connected to the transmitter circuitry of the catheter tracer.

Four discrete LEDs 60 are mounted on the underside of the slotted template 48 in a circular array. Each LED 60 is positioned ninety degrees from its adjacent LEDs. As will be described in greater detail, these LEDs will be strobed on at predetermined times. Light from the LEDs 60 will pass through the slot 52 in the disc portion of the template. The light from the LEDs will pass through the slot and will be projected as an image on the face lens 16 disposed above the slotted template 48. The projected image 22 formed by the LEDs 60 will be in the shape of an elongated bar or line, which image is visible to the physician. The LEDs 26 of the proximity display 20, as well as the digit LEDs 24 of the distance indicator, are also positioned below the face lens 16 of the probe and viewable through the lens.

FIGS. 5 and 6 show the locator wire 4 and a receive coil 6 located near or on the free end of the wire. The locator wire 4 is preferably formed as a single strand wire 62 such as 0.012 inch diameter piano wire. The receive coil 6 is preferably formed by winding 800 turns of #43 AWG wire 64 around the tip portion of the piano wire 62. The tip portion of the piano wire 62 may be annealed to increase its permeability.

The lead wires 66 which carry the received signal from the receive coil 6 along the locator wire 4 are wrapped in a helical manner along the locator wire to a connector P1 which plugs into the hand-held probe 2. Each of the two lead wires 66 is wrapped in opposite directions, one following a right-hand helix and the other following a left-hand helix. Both lead wires are wrapped with similar spacing. This configuration aids in the cancellation of any electromagnetic interference which is induced in the lead wires 66. The receive coil 6 and lead wires 66 may be sprayed with a urethane varnish or the like to maintain their wrapped configuration about the locator wire 4.

Although not shown but envisioned to be within the scope of the invention, a catheter or the catheter guide wire may be formed with the receive coil located at its free end, instead of using a locator wire. If the locator wire is used, the medical team periodically removes the guide wire during the catheter insertion operation, and inserts the locator wire 4 in its place, in order to determine the present location and orientation of the catheter within the patient's body.

The electronic circuitry of the catheter tracer of the present invention will now be described in greater detail, and with reference to FIGS. 7-9 of the drawings.

FIG. 7 shows, in block diagram form, the relationship of the various functional blocks of the electronic circuitry. This relationship can best be seen by tracing the transmit signal through the circuitry, starting with the transmitter portion of the catheter tracer.

The transmitter includes an oscillator 68 which generates a transmit signal preferably of constant amplitude and a carrier frequency of approximately 2,200 hertz. The output signal of the oscillator 68 is provided to a modulator 70, whose function will be described in greater detail, and the modulator's output signal is provided to the transmit coil 18.

The receiver of the catheter tracer includes a receive coil 6, as mentioned previously, which is mounted on the tip of the catheter, its guide wire or the locator wire 4. As the transmit coil 18 is brought into proximity with the receive coil 6 (at a distance of approximately 16 centimeters between the two coils), the receive coil 6 begins to receive the signal sent by the transmit coil 18 due to magnetic coupling between the two, which causes a voltage and current to be induced in the receive coil. The amplitude of the induced voltage and current is a function of the orientation of the transmit coil with respect to the receive coil and the distance between the two coils.

Figure 9A:
FIGS. 9a through 9d are various signal waveforms associated with the circuitry of the catheter tracer of the present invention.

When the longitudinal axes of the two coils are in parallel, the magnetic coupling between the two is the greatest, and the maximum current and voltage is induced in the receive coil 6. When the axes of the two coils are orthogonal, the induced current and voltage in the receive coil 6 drops to a minimum level. The electrical current and voltage amplitude follows a periodic rise and fall with a steady rotational motion of the transmit coil 18. The rotation of the transmit coil 18 amplitude modulates the 2,200 hertz carrier transmit frequency of the transmitted signal (this modulation is not performed by the transmitter modulator 70 mentioned previously). The signal induced in the receive coil 6 is a 2,200 hertz signal which increases and decreases in amplitude in a periodic fashion at a rate of about 10 hertz. The resulting waveform of the received signal induced in the receive coil is illustrated by FIG. 9a.

The receiver has additional circuitry for processing the signal induced in the receive coil 6. This circuitry is preferably housed in the hand-held probe 2 with the transmitter. The receiver processing circuitry includes an amplifier 72 which is connected to the receive coil 6. The amplifier 72 amplifies the received signal and preferably has a gain of approximately 68. In its preferred form, the receiver amplifier 72 has a differential input which is connected to the two leads of the receive coil (through appropriate mating connectors P1 and J1), thereby reducing the effects of common mode noise at the amplifier's input.

Figure 9B:
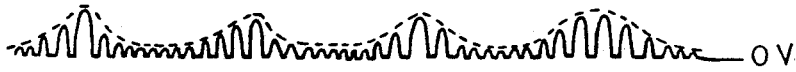
Figure 9D:
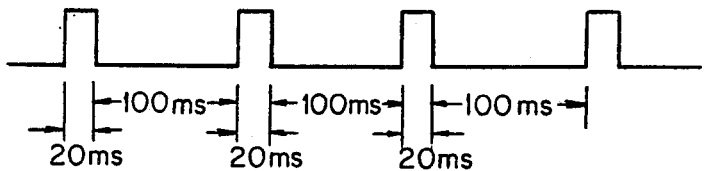

The receiver processing circuitry further includes a rectifier circuit 74 to which the amplified signal is provided. The rectifier circuit 74 rectifies the signal to provide an output signal which has only a positive component. The output signal of the rectifier is shown in FIG. 9b.

The receiver processing circuitry further includes a low pass filter or integrator circuit 76, which receives and averages the rectified output signal of the rectifier circuit 74 and provides an output signal which is, essentially, a voltage level having an amplitude which varies with the peak amplitude of the rectified output signal and which changes slowly and inversely with the strength of the received signal.

The receiver processing circuitry may also include a unity gain, buffer amplifier 78 which is connected to the low pass filter circuit 76 and which "buffers" the filter circuit by providing a high impedance load to the filter circuit. The buffer amplifier 78 provides its output signal to the transmitter modulator 70 and to the display circuitry.

The transmitter modulator 70 creates a 2,200 hertz carrier signal having a strength which is inversely proportional to the strength of the received signal, due to the negative feedback of the received signal through the differential amplifier 72, rectifier circuit 74, filter circuit 76 and the buffer amplifier 78 to the transmitter modulator 70. The negative feedback of the received signal increases the operating range of the catheter tracer by reducing the extreme variation in amplitude of the received signal over varying distances and, in effect, linearizes the received signal strength over the distance between the transmit coil 18 and the receive coil 6.

As mentioned previously, the catheter tracer further includes circuitry and an associated display for indicating to the physician the orientation of the catheter within the patient's body. The catheter orientation circuitry effectively translates the time relation of the amplitude peaks of the received signal into a display of the orientation of the receive coil mounted on the catheter, guide wire or locator wire tip. The orientation circuitry includes a pulse amplifier and shaper circuit 80 which is provided with the output signal of the rectifier circuit 74. The pulse amplifier and shaper circuit 80 provides gain and an offset adjustment to the rectified signal, and eliminates the 2,200 Hertz carrier frequency from the signal. The output signal from the pulse amplifier and shaper circuit 80 is, effectively, the amplified envelope of the rectified signal, adjustable in offset.

The output signal of the pulse amplifier and shaper circuit is provided to a monostable multivibrator 82 and is adjusted in offset to trigger the monostable multivibrator at the peaks of the envelope, which correspond to the peaks in the received signal. The multivibrator 82 provides a logic output signal in the form of a pulse each time a peak in the received signal occurs. The pulse created is a square wave pulse, which is preferably 20 milliseconds in duration. This pulse is provided for turning on the high intensity light emitting diodes 60, which are strobed on whenever the pulse is present. The pulse occurs ten times per second, and is synchronized to the time the transmit coil 18 is aligned with the receive coil 6.

The output signal of the monostable multivibrator 82 is connected to a drive circuit 84, which in turn drives the strobe light emitting diodes (LEDs) 60, which are connected in parallel. The LEDs 60 are, in effect, strobed on for a predetermined duration whenever a pulse is generated by the monostable multivibrator. The light of the high intensity light emitting diodes 60 shines through the slot 52 formed in the rotating slotted template 48, which slot projects an image of a bar or line 22 on the face lens 16 of the hand-held probe. The image appears to be frozen in time in a position indicative of the orientation of the receive coil 6.

Also as mentioned previously, the catheter tracer of the present invention includes a proximity display circuit and a digital voltmeter circuit with its associated numeric "distance" display. The proximity display circuit includes a range and offset adjust circuit 86, which is provided with the output signal from the buffer amplifier 78.

The range and offset adjust circuit 86 preferably has a gain of approximately three and allows a variable DC offset to be introduced to the buffer amplifier's output signal to adjust the proximity bar display 20, which indicates the received signal strength, so that the LED segment of the bar display which indicates the lowest signal level remains illuminated for small received signal levels. The output of the range and offset adjust circuit 86 is provided to a driver circuit 88, which drives the proximity LEDs 26.

The digital voltmeter circuit includes a range adjust circuit 90 to which the buffer amplifier's output signal is provided. The output signal from the range adjust circuit 90 is provided to an analog-to-digital converter circuit 92, having outputs which drive the LED digit display 24. The voltmeter circuit of the tracer provides a numeric display of the distance between the hand-held probe and the receive coil in centimeters.

Figure 8A:
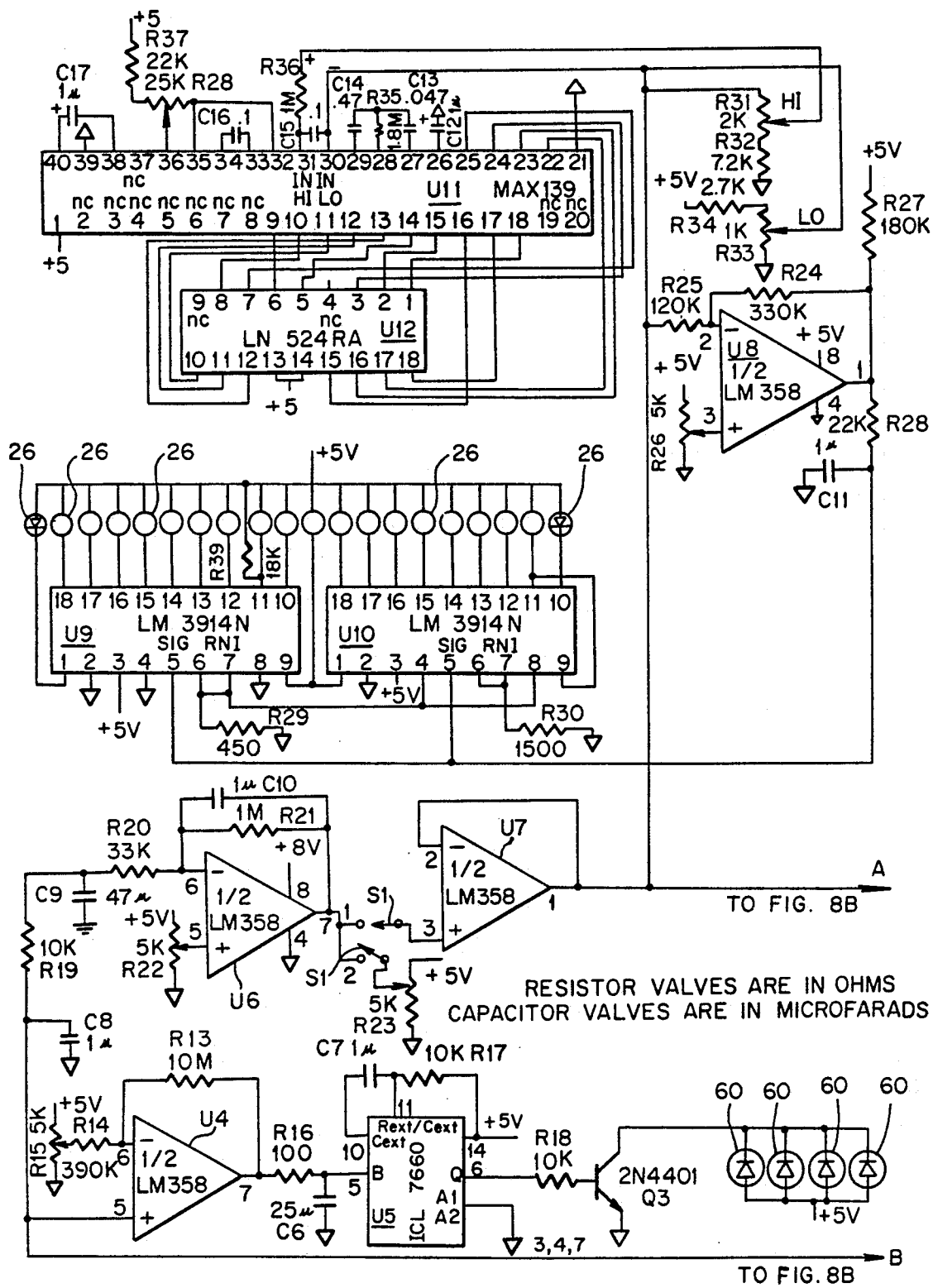

FIG. 8 schematically shows a preferred form of the electronic circuitry of the catheter tracer. The actual values and part numbers of the components used in the electronic circuitry shown in FIG. 8 are for illustrative purposes only, and to facilitate an understanding of the invention. However, alternative components, and values for these components, may be substituted by one skilled in the art to provide the same or similar results. The numbers positioned adjacent to the integrated circuits shown in FIG. 8 represent the pin numbers of the circuits.

The oscillator 68 of the transmitter preferably is formed from a CMOS timer/counter circuit U1, such as Intersil, Inc. integrated circuit ICM 7242 which internally consists of an RC oscillator followed by an eight bit binary counter. The trigger (TR) input of the integrated circuit U1 is connected to a voltage level of +5 volts through a fixed resistor R1, which causes the integrated circuit U1 to output a square wave with a 50% duty cycle on the "+2" output terminal. The "Vss" and reset (R) inputs are grounded, and a capacitor C1 is connected between ground and the "RC" input. The "$V_{DD}$" input is connected to +5 volts and to one end of a potentiometer R2 through a fixed resistor R3. The other end of the potentiometer R2 and the wiper of the potentiometer are connected to the "RC" input.

The potentiometer R2 allows the frequency of the output signal of the oscillator 68 to be tuned to match the resonant frequency of the transmit coil 18. The combination of the capacitor C1 and the resistance of the potentiometer R2 and the fixed resistor R3 sets the RC time constant for the oscillator circuit U1.

The transmitter modulator 70 includes an NPN transistor Q1 and a field effect transistor (FET) Q2. The "+2" output of the oscillator circuit is connected to the base of transistor Q1 through a base resistor R4. The emitter of transistor Q1 is connected to ground, and the collector is connected to the gate of transistor Q2. The source of transistor Q2 is grounded, and the drain of transistor Q2 is connected to one lead of the rotating transmit coil 18 through a diode D1 and one slip ring 58. The collector of transistor Q1 is also connected to the output signal of the buffer amplifier 78 (see U7 in FIG. 8) through a resistor R5.

Resistor R4 limits the base current which flows into transistor Q1. Transistor Q1 allows the gate of transistor Q2 to have a potential equal to the output of the buffer amplifier U7 or to be held at ground potential. Transistor Q1 thus provides a square wave signal on the gate of transistor Q2 of approximately 2,200 hertz, which signal has a high level equal to the voltage at the output of the buffer amplifier U7, and a low level which is approximately equal to ground potential.

The FET transistor Q2 will conduct to a greater or lesser degree upon application of the high level portion of the signal provided on its gate. Transistor Q2 provides a square wave signal to the transmit coil 18.

The transmit coil 18 is connected at its other end through a slip ring 58 preferably to +8 volts. Furthermore, a capacitor C2 is connected in parallel with the transmit coil. The transmit coil, shunted by the capacitor C2, is tuned to form a high "Q" resonant circuit. The square wave signal provided to the coil 18 is filtered by the tuned circuit (defined by the capacitor C2 and the inductance of the coil) to the fundamental frequency of the square wave and the harmonics are suppressed, their energy being converted to energy at the fundamental frequency. This process allows the voltage across the transmit coil 18 to reach as much as 90 volts at the fundamental frequency when the coil is driven by the +8 volt source.

As mentioned previously, the transmit coil 18 is rotated by a motor 40, which is connected between +2.5 volts and ground.

The transmit coil 18 couples to the receive coil 6 by mutual inductance. The leads of the receive coil are connected to a connector P1 which plugs into a mating connector J1 located on the handle 8 of the hand-held probe.

As described above, the transmit coil 18 is preferably rotated at 300 rpm or 5 cycles per second. The amount of induced coupling in the receiver is a function of the distance between the two coils and the orientation of one with respect to the other. The amount of coupling will be increasing and decreasing at twice the rate of rotation of the transmit coil, since every time the transmit coil rotates 180°, the transmit coil and the receive coil will be in alignment such that maximum signal will be induced in the receive coil.

Connector J1 is connected to the non-inverting (+) input and the inverting (−) input (through a resistor R6) of a differential amplifier U2 so that the signal induced in the receive coil 6 can be amplified. The differential amplifier U2, which may be integrated circuit LF357 manufactured by National Semiconductor Co., defines the receiver amplifier 72 discussed previously in the preferred form of the invention. The electrical components associated with the differential amplifier U2 includes a capacitor C3 which shunts resistor R6 to stabilize the high gain amplifier, a resistor R7 from the non-inverting (+) input to ground to balance the inputs for offset currents within the amplifier, and a feedback resistor R8 between the output of the amplifier and the inverting (−) input which, in combination with resistor R6, sets the gain of the amplifier preferably at −68.

The rectifier circuit 74 is preferably a precision half-wave rectifier comprising an operational amplifier U3, which may be integrated circuit LM307 manufactured by National Semiconductor Co., and associated diodes and resistors. The output signal of the receiver amplifier U2 is coupled to the inverting (−) input of the rectifier's operational amplifier U3 through a capacitor C4 and a resistor R9 connected in series, the capacitor C4 acting as a DC blocking capacitor. A feedback diode D2 is arranged with its anode connected to the inverting (−) input of the amplifier and its cathode connected to the output. The output of the amplifier U3 is also connected to the anode of another diode D3, whose cathode provides the rectified output signal of the rectifier circuit. The cathode of diode D3 is connected to the parallel combination of a capacitor C5 and a resistor R10 which are also connected to the inverting input of the amplifier. Resistors R11 and R12 are connected in series between +5 volts and ground, with their series connection connected to the non-inverting (+) input of the amplifier U3. Resistors R11 and R12 form a resistor divider network to provide a certain amount of offset voltage adjustment for the amplifier.

Preferably resistors R9 and R10 ar of equal value to provide a gain of −1 for signals below 0 volts at the rectifier side of coupling capacitor C4. This produces a positive output signal at the cathode of diode D3. When the output signal from the receiver amplifier U2 is positive, the output of the rectifier circuit U3 is 0 volts plus a small offset which is produced by the divider network of resistors R11 and R12. The waveform of the output signal from the precision half-wave rectifier (i.e., at the cathode of diode D3) is shown in FIG. 9b.

The output signal of the rectifier circuit 74 is applied to the input of the pulse amplifier and shaper circuit 80. The amplifier and shaper circuit basically includes an operational amplifier U4 having a feedback resistor R13 connected between the output and the inverting (−) input of the amplifier, and an input resistor R14 connected between the inverting (−) input and the wiper of a potentiometer R15. The legs of potentiometer R15 are connected between ground and +5 volts. The non-inverting (+) input of the operational amplifier U4 receives the output signal of the rectifier circuit 74. The associated resistors R13, R14 are chosen to provide preferably a gain of 4 through the amplifier. The potentiometer R15 provides an adjustable offset at the output of the amplifier U4. Amplifier U4 may be integrated circuit LM358 manufactured by National Semiconductor Co.

The output of the amplifier U4 is connected to a resistor R16 and a capacitor C6 connected to ground. Resistor R16 and capacitor C6 eliminate the 2,200 hertz carrier signal which still remains.

Figure 9C:

The connecting point between resistor R16 and capacitor C6 is provided to the "B" trigger input of a monostable multivibrator U5. Because the resistor R16 and capacitor C6 effectively define an envelope detector by eliminating the carrier frequency, the monostable multivibrator U5 will trigger at the peaks of the envelope. To ensure the multivibrator's proper triggering, potentiometer R15 is adjusted to offset the signal provided on the "B" trigger input. FIG. 9c illustrates the signal at the trigger input of the multivibrator.

The monostable multivibrator U5 is preferably a Schmitt-trigger type to allow gitter-free triggering, such as integrated circuit SN74121 manufactured by Texas Instruments Co. Its "B" input is a Schmitt trigger input and is connected to resistor R16. The monostable multivibrator includes associated circuitry to adjust the duration of its output pulse. A resistor R17 is connected between the $R_{ext}/C_{ext}$ input and +5 volts, and a capacitor C7 is connected between the same input and the $C_{ext}$ input. The "A1" and "A2" inputs are grounded. The values of resistor R17 and capacitor C7 are chosen to provide a pulse length of approximately 20 milliseconds. The monostable multivibrator U5 provides a pulsed output signal on its "Q" output. A high logic level pulse from monostable multivibrator U5 occurs at each peak of the envelope of the output signal from the amplifier U4, and the logic level of the output signal from the multivibrator U5 remains low for the remaining 180 milliseconds until the next peak in the envelope occurs.

The output signal of the monostable multivibrator U5 is applied to the base of an NPN transistor Q3 through a current limiting resistor R18. Transistor Q3 drives the high intensity "strobe" LEDs 60. More specifically, the emitter of transistor Q3 is grounded and the collector of transistor Q3 is connected to the cathodes of the strobe LEDs 60, whose anodes are connected together and to +5 volts.

The result is that the high intensity strobe LEDs 60 will illuminate for 20 milliseconds, the duration of the positive portion of the output signal from the monostable multivibrator U5. This period that the LEDs will "flash" is coincident with the transmit coil 18 being aligned with the receive coil 6.

The output signal from the precision rectifier circuit 74 is also provided to a low pass filter circuit 76. As shown in FIG. 8, the low pass filter is preferably formed from an operational amplifier U6, such as integrated circuit LM358, configured as a single pole filter with a very low frequency 3dB cutoff point, in association with a collection of resistors and capacitors.

More specifically, the rectified output signal is provided to one side of a resistor R19 and to a capacitor C8 to ground. The other side of resistor R19 is connected to another capacitor C9 connected to ground. Capacitor C9 is connected to an input resistor R20, which is connected at its other end to the inverting (−) input of the filter operational amplifier U6. The output of the amplifier U6 is connected to the inverting (−) input through the parallel combination of a feedback resistor R21 and a feedback capacitor C10.

The non-inverting (+) input of operational amplifier U6 is connected to the wiper arm of a potentiometer R22, having one end connected to ground and the other end connected to +5 volts. Potentiometer R22 provides an adjustable offset to the filtered output signal from amplifier U6.

The associated components of the filter amplifier U6 are chosen so that the DC gain of the filter is equal to approximately −3, with an adjustable offset. At 2,200 hertz, the gain of the amplifier is reduced to approximately zero due to the relatively low capacitive reactance of capacitor C10 in relation to the resistance of input resistor R20 at the inverting (−) input of amplifier U6.

The output signal of filter U6 is provided to a switch S1 which allows the operator to simulate an input to the buffer amplifier 78, and thereby set the sensitivity and range of the proximity bar display and the digital voltmeter, as will be explained in greater detail. When the switch S1 is in a first position (i.e., position "1" in FIG. 8), a potentiometer R23 is disconnected from the circuit, and the output signal from the filter amplifier U6 is connected to the buffer amplifier 78. When the switch S1 is in a second position (i.e., position "2"), the filter is disconnected from the buffer amplifier, and the potentiometer R23 is connected to provide a DC signal to the buffer amplifier. Potentiometer R23 has its wiper connected to the switch, one end connected to ground and the other end connected to +5 volts.

The output of the switch S1 is connected to the non-inverting (+) input of an operational amplifier U7, which may also be an LM358 integrated circuit and which has its output connected to the inverting (−) input so as to provide unity gain. Amplifier U7 thus defines a unity gain, non-inverting buffer amplifier 78 which creates a current source buffer that feeds the display circuits and the transmitter modulator 70.

Figure 10:
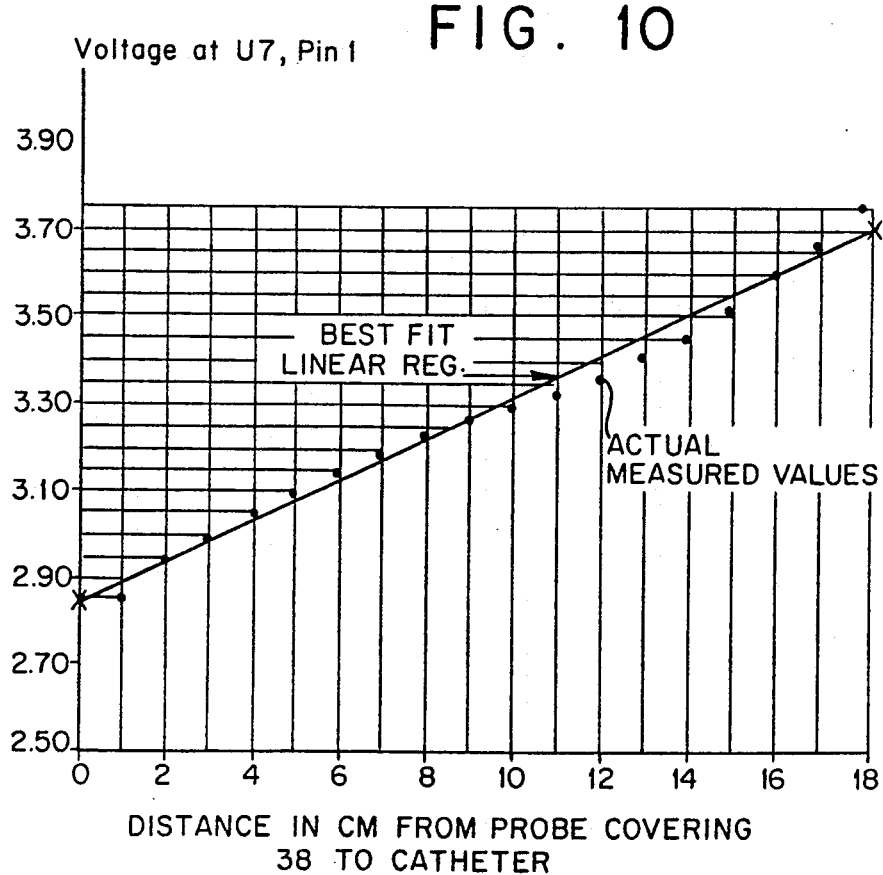
FIG. 10 is a graph of voltage versus distance, showing the correlation between the amplitude of the received signal and the distance between the hand-held probe and the tip of the catheter locator wire.

The output signal of the buffer amplifier U7 is applied to fixed series resistor R5, discussed previously, which limits the current when modulator transistor Q1 is turned on. The output signal of the buffer amplifier 78 is, in effect, a DC level which is inversely proportional to the strength of the signal received by the receive coil. Since the gain of the receiver amplifier 72 is negative, the gain of the rectifier circuit 74 is negative, and the gain of the filter circuit 76 is negative, and because the gain of the buffer amplifier 78 is positive, the total gain of the signal from the receive coil to the buffer amplifier output is negative (that is, three negative gains and one positive gain). This negative feedback from the receiver to the transmitter allows large variations in received signal strengths to be contained within a narrow voltage range, and further provides a direct proportional relationship between the received signal strength and the distance between the receive coil 6 and the transmit coil 18. This direct relationship may be made substantially linear, as shown in FIG. 10, as will be described in greater detail.

The output signal of the buffer amplifier 78 is further provided to the bar display circuitry and to the digital voltmeter.

More specifically, the output signal from the buffer optional amplifier U7 is provided to a range and offset adjust amplifier 86 of the bar display circuitry. The range and offset adjust amplifier 86 includes an operational amplifier U8, such as an LM358 integrated circuit, having its output connected to its inverting (−) input through a feedback resistor R24, and an input resistor R25 connected between the output of the buffer amplifier U7 and the inverting (−) input of the operational amplifier U8. The non-inverting (+) input of the operational amplifier U8 is connected to the wiper of a potentiometer R26, the potentiometer R26 having its terminals tied between +5 volts and ground. A pull-up resistor R27 may be connected between the output of the operational amplifier U8 and +5 volts.

Potentiometer R26 allows adjustment to be made to the offset voltage of the range adjust operational amplifier U8. The gain of the range adjust amplifier U8 is set by the ratio of the feedback resistor R24 to the input resistor R25. The values of resistor R24 and resistor R25 are selected to amplify the signal from the buffer amplifier U7 so that most of the LEDs 26 of the bar display 20 will be used over the full range of the catheter tracer.

The output signal of the range and offset adjust operational amplifier U8 is provided to a filter circuit having a resistor R28 and a capacitor C11 connected between the resistor R28 and ground. Resistor R28 and capacitor C11 will slow the response of the output signal of the range and offset adjust operational amplifier U8. This intentional slowing of the signal stabilizes the bar display by slightly dampening its response to changes in the received signal strength.

The output of the filter circuit, i.e., the ungrounded side of capacitor C11, is connected to the signal (SIG) inputs of a pair of bar display driver circuits U9, U10, each of which may be integrated circuit LM3914 manufactured by National Semiconductor Co. Each output (i.e., pin nos. 1 and 10–18) of the bar display driver circuits U9, U10 is connected to the cathode of a respective proximity LED 26, whose anode is connected to +5 volts.

Each display driver circuit U9, U10 in this embodiment is capable of controlling the illumination of 10 proximity LEDs 26. The values of the resistors R29 and R30 connected between the $R_{NI}$ input of each circuit and ground determine the input voltage which is required to cause each LED segment 26 of the bar display 20 to illuminate. In the present embodiment, the values of resistors R29 and R30 allow a smooth and continuous bar display in which each LED segment is lighted in succession as a function of the amplitude of the input signal to the two bar display driver circuits U9, U10. Each successive segment is illuminated by an increase in the bar display driver's input signal's amplitude of approximately 7 millivolts. The range of the bar display circuit is from about 10 millivolts for a single segment to be illuminated, up through 150 millivolts, at which level all 20 segments are illuminated. The offset voltage adjust potentiometer R26 of the range and offset adjust amplifier U8 is used to calibrate this voltage range to the signal strength which is received at distances in the range of one centimeter to 16 centimeters. A resistor R39 is connected between +5 volts and pin 11 on the second bar display driver U9. The graph of FIG. 10 indicates the relationship between the distance from the receive coil 6 to the transmit coil 18 and the voltage which appears at the output of the buffer amplifier U7.

The output signal of the buffer operational amplifier U7 is also provided to the digital voltmeter circuit. More specifically, the output of the buffer amplifier U7 is connected to one end of a potentiometer R31, whose other end is connected to a fixed resistor R32, which is connected to ground. The wiper of potentiometer R31 is connected to the "IN HI" input of a 3½ digit A/D converter and LED display driver circuit U11, such as integrated circuit MAX 139 manufactured by Maxim Integrated Products. Another potentiometer R33 is connected between ground and a fixed resistor R34, connected to +5 volts, and has its wiper connected to the "IN LO" input of the same circuit U11. The potentiometers R31 and R33 allow the digital voltmeter portion of the circuit to be calibrated in units per centimeter.

More specifically, the voltage level which is provided by the buffer amplifier U7 at a distance of 16 centimeters is, in this embodiment, the greatest voltage level which the digital voltmeter circuit is set to measure and display as a value in distance. The buffer amplifier output signal is inversely proportional to the distance between the transmit coil 18 and the receive coil 6. Therefore, the nearer the receive coil is to the transmit coil, the smaller the voltage is at the buffer amplifier output. By adjusting the potentiometer R31 until the associated LED digital display 24 displays the number "16", the high end of the distance meter can be calibrated. The low value of the digital voltmeter can be calibrated by adjusting the potentiometer R33 so that the number "1" appears on the LED digital display 24 when the receive coil and the transmit coil are one centimeter apart.

The LED display 24 is preferably a two-digit integrated circuit U12, such as LN524RA manufactured by Panasonic Corp., having the segments interconnected to the corresponding outputs of the A/D converter and LED driver circuit U11, as shown in FIG. 8.

The A/D converter circuit U11 includes associated external components, such as capacitors C12 through C17, resistors R35 through R37 and potentiometer R38, all of which are connected to the circuit in a manner known to those skilled in the art and as illustrated by FIG. 8, and as shown in the Maxim Integrated Products specification literature for the MAX 139 circuit.

The catheter tracer of the present invention also includes a power supply circuit. The power supply circuit includes a charging jack J2, which is mounted on the handheld probe casing and in particular on the handle 8. The charging jack J2 allows for an external power source to be applied to the hand-held probe to recharge the nickel cadmium rechargeable batteries 31 contained therein.

An on/off switch S2 disconnects the batteries from the power supply circuitry when the unit is not in use. When the switch S2 is closed, power is provided to a voltage regulator integrated circuit U13 and to a "low battery" detection circuit U14. The low battery detection circuit U14, which may be integrated circuit ICL7665 manufactured by Maxim Integrated Products, compares the voltage at the switch S2 to a threshold voltage provided by a resistor divider network comprising resistors R40 and R41, and will illuminate a "low battery" indicator 94 comprising an LED connected between the output of the low voltage circuit U14 and the voltage on the switch S2, through a series current limiting resistor R42.

The voltage regulator integrated circuit U13, which may be integrated circuit 7805 manufactured by National Semiconductor Co., converts an unstable +8 volts provided by the NiCad batteries 31 to a highly stable +5 volts which will not vary with load fluctuations until such time as the batteries fall below the voltage required for proper operation of the regulator circuitry. Capacitors C18 and C19 shunt the input and output, respectively, of the voltage regulator U13 to provide stability and to prevent oscillations. The voltage regulator output supplies a regulated +5 volt output to all of the circuitry which requires such a source.

The power supply circuit of the catheter tracer also includes a voltage inverter integrated circuit U15, such as circuit ICL7660 manufactured by Maxim Integrated Products, which circuit provides a −5 volt source to those amplifiers and other devices which require a dual voltage source. The voltage inverter U15 includes an associated capacitor C20, connected to the ±CAP inputs in a well known manner and as described in the Maxim Integrated Products specification literature for the circuit, as well as a filter capacitor C21 at its output to maintain a steady and stable −5 volt source.

A +2.5 volt source is created by a transistor Q4 in a common base configuration. Resistors R43 and R44 connected to the base of the transistor and between the output of the voltage regulator U13 and ground, provide proper biasing for the transistor Q4. The collector of transistor Q4 is connected to the output of the voltage regulator U13, and the emitter of transistor Q4 provides +2.5 volts for the circuitry of the cathode tracer. This source provides the voltage and current required by the DC motor 40 which rotates the transmit coil 18 and the slotted template 48.

The catheter tracer of the present invention provides a way of determining the location and orientation of a medical object, and in particular a catheter, which has been inserted into a patient's body. The distance and orientation of the catheter can be determined quickly and accurately, and the catheter's movement in the patient's body as it is being inserted may be tracked.

The catheter tracer of the present invention is simple in construction and inexpensive to manufacture, and is quite portable and lightweight and may be formed as a hand-held probe, as described. The use of the catheter tracer minimizes the need to employ x-rays to determine whether the path which the catheter has followed is the intended path.

It is apparent to one skilled in the art, and envisioned to form part of the present invention, that similar results will occur by having the transmit coil mounted on the catheter, guide wire or locator wire, and the receive coil situated in the hand-held probe and rotated—in other words, substituting one coil for the other.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. Apparatus for determining the location of an object adapted to be inserted into the body of a patient, which comprises:

a transmitter, the transmitter including an oscillator for generating a transmit signal, and a transmit coil coupled to the oscillator for transmitting a signal corresponding to the transmit signal;

a receiver, the receiver including a receive coil for receiving the signal transmitted by the transmitter by mutual inductance between the two coils, means for processing the signal received by the receive coil, one of the transmit coil and the receive coil being situated on the object adapted to be inserted into the patient's body, and the other of the receive coil and the transmit coil being located externally to the patient's body, the processing means providing an output signal which varies in accordance with the strength of the signal received by the receive coil and detecting the distance the transmit coil is form the receive coil based on the strength of the signal received by the receive coil, the receiver further including display means coupled to the processing means for indicating at least the relative distance which the transmit coil is from the receive coil, whereby the location of the object adapted to be inserted into the patient's body may be located; and means for controlling the strength of the signal transmitted by the transmit coil in response to the output signal of the processing means of the receiver, the control means being operatively coupled to the processing means.

2. Apparatus for determining the location of an object adapted to be inserted into the body of a patient, which comprises:

a transmitter, the transmitter including an oscillator, the oscillator generating a first signal, means responsive to the first signal of the oscillator for controlling the level of the first signal in accordance with the strength of a signal received by a receiver operatively linked to the transmitter and providing a second signal, and a transmit coil responsive to the second signal and transmitting a third signal corresponding to the second signal; and a receiver, the receiver including a receive coil separated from the transmit coil by a distance and for receiving the signal transmitted by the transmit coil and providing a received signal, processing means for processing the received signal to determine the distance between the receive coil and the transmit coil and for providing a processed signal, the control means being operatively coupled to the processing means of the receiver and responsive to the processed signal, and display means responsive to the processed signal for indicating at least the relative distance between the transmit coil and the receive coil, one of the transmit coil and the receive coil being situated on the object adapted to be inserted into the patient's body, and the other of the receive coil and the transmit coil being located externally to the patient's body, whereby the location of the object adapted to be inserted into the patient's body may be determined.

3. Apparatus for determining the orientation of an object adapted to be inserted into a patient's body, which comprises:

a transmitter oscillator, the transmitter oscillator generating a first signal;

a transmit coil situated externally to the patient's body, the transmit coil being responsive to the first signal and transmitting a second signal corresponding to the first signal;

means for rotating the transmit coil in a direction transverse to a longitudinal axis of the transmit coil;

a receive coil situated on the object adapted to be inserted into the patient's body, the receive coil receiving the second signal transmitted by the rotating transmit coil and providing a third signal in response thereto;

rectifying means responsive to the third signal for providing a rectified fourth signal;

strobe means for providing strobes of light in response to the rectified fourth signal; and bar image forming means operatively cooperating with the strobe means for providing an image of a bar, the bar image being aligned with a longitudinal axis of the receive coil and thereby being indicative of the orientation of the object on which the receive coil is situated.

4. The apparatus as defined by claim 3, wherein the bar image forming means includes a slotted template, the slotted template being synchronously rotatable with the transmit coil and having an elongated slot formed therein, the slot being aligned with the longitudinal axis of the transmit coil.

5. The apparatus as defined by claim 4, wherein the slotted template of the bar image forming means is coupled to the transmit coil rotating means so as to rotate with the transmit coil.

6. Apparatus for determining the location of an object adapted to be inserted into a patient's body, which comprises:

a transmitter oscillator, the transmitter oscillator generating a first signal;

means responsive to the first signal for controlling the level of the first signal in accordance with the strength of a signal received by a receiver operatively linked to the transmitter oscillator and providing a second signal;

a transmit coil situated externally to the patient's body, the transmit coil being responsive to the second signal and transmitting a third signal corresponding to the second signal;

a receive coil situated on the object adapted to be inserted into the patient's body, the receive coil receiving the third signal transmitted by the transmit coil and providing a fourth signal in response thereto;

rectifying means responsive to the fourth signal for providing a rectified fifth signal;

filter means responsive to the rectified fifth signal for providing a filtered sixth signal in response thereto, the control means being operatively coupled to the filter means and responsive to the filtered sixth signal and controlling the level of the second signal in response thereto; and means for providing an indication of the location of the object adapted to be inserted into the patient's body, the location indicating means being responsive to the filtered sixth signal.

7. The apparatus as defined in claim 6, wherein the object location indicating means includes means for providing a bar display indicating the relative proximity of the transmit coil to the receive coil, the bar display means being responsive to the filtered sixth signal.

8. The apparatus as defined in claim 6, wherein the object location indicating means includes means for providing a numeric display of the distance between the receive coil and the transmit coil, the distance display means being responsive to the filtered sixth signal.

9. The apparatus as defined in claim 6, which further determines the orientation of the object in the patient's body, and which further comprises:

means for rotating the transmit coil in a direction transverse to a longitudinal axis of the transmit coil;

strobe means for providing strobes of light in response to the rectified fifth signal; and bar image forming means, the bar image forming means including a slotted template synchronously rotatable with the transmit coil and having an elongated slot formed therein, the slot being aligned with the longitudinal axis of the transmit coil, the bar image forming means operatively cooperating with the strobe means to provide an image of a bar, the bar image being aligned with a longitudinal axis of the receive coil and thereby being indicative of the orientation of the object on which the receive coil is situated.

10. Apparatus for determining the location and orientation of an object adapted to be inserted into a patient's body, which comprises:

a transmitter oscillator, the transmitter oscillator generating a first signal;

a transmitter modulator responsive to the first signal and providing a modulated second signal;

a transmit coil situated externally to the patient's body, the transmit coil being responsive to the modulated second signal and transmitting a third signal corresponding to the second signal;

means for rotating the transmit coil in a direction transverse to a longitudinal axis of the transmit coil;

a receive coil situated on the object adapted to be inserted into the patient's body, the receive coil receiving the third signal transmitted by the rotating transmit coil and providing a fourth signal in response thereto;

rectifying means responsive to the fourth signal for providing a rectified fifth signal;

filter means responsive to the rectified fifth signal for providing a filtered sixth signal in response thereto, the transmitter modulator being further responsive to the filtered sixth signal and controlling the level of the modulated second signal in response thereto;

strobe means for providing strobes of light in response to the rectified fifth signal;

bar image forming means, the bar image forming means including a slotted template synchronously rotatable with the transmit coil and having an elongated slot formed therein, the slot being aligned with the longitudinal axis of the transmit coil, the bar image forming means operatively cooperating with the strobe means to provide an image of a bar, the bar image being aligned with a longitudinal axis of the receive coil and thereby being indicative of the orientation of the object on which the receive coil is situated; and means for providing an indication of the location of the object adapted to be inserted into the patient's body with respect to the transmit coil, the location indicating means being responsive to the filtered sixth signal.

11. A method for locating an object inserted into a patient's body, which comprises the steps of:

generating a first signal;

transmitting the first signal from a transmit coil located externally to the patient's body;

receiving the transmitted signal by a receive coil situated on the object in the patient's body;

rectifying the signal received by the receive coil;

filtering the rectified signal and providing a filtered signal;

controlling the level of the first signal in response to the filtered signal; and displaying an indication of the relative location of the object from the transmit coil in response to the filtered rectified signal.

12. A method for determining the orientation of an object inserted into a patient's body, which comprises the steps of:

transmitting a signal from a transmit coil situated externally to the patient's body;

rotating the transmit coil in a direction transverse to a longitudinal axis of the transmit coil;

receiving the transmitted signal by a receive coil situated on the object inserted into the patient's body;

rectifying the received signal;

providing strobes of light in response to the rectified received signal; and forming an image of a bar in response to the strobes of light, the bar image being aligned with a longitudinal axis of the receive coil and thereby being indicative of the orientation of the object on which the receive coil is situated.

13. A method for determining the location and orientation of an object inserted into a patient's body, which comprises the steps of:

generating a first signal;

modulating the first signal;

transmitting the modulated signal from a transmit coil situated externally to the patient's body;

rotating the transmit coil in a direction transverse to a longitudinal axis of the transmit coil;

receiving the transmitted signal by a receive coil situated on the object inserted into the patient's body;

rectifying the received signal;

filtering the rectified received signal, the first signal being modulated in response to the filtered and rectified received signal;

providing strobes of light in response to the rectified and filtered received signal;

forming an image of a bar in response to the strobes of light, the bar image being aligned with a longitudinal axis of the receive coil and thereby being indicative of the orientation of the object on which the receive coil is situated; and providing an indication of the location of the object with respect to the transmit coil in accordance with the strength of the filtered and rectified received signal.

* * * * *